US009662101B2

(12) United States Patent
Thompson et al.

(10) Patent No.: US 9,662,101 B2
(45) Date of Patent: May 30, 2017

(54) SELF-RETAINING RETRACTOR

(71) Applicants: Thomas R. Thompson, Akron, OH (US); Bradley T. Webb, Broadview Heights, OH (US)

(72) Inventors: Thomas R. Thompson, Akron, OH (US); Bradley T. Webb, Broadview Heights, OH (US)

(73) Assignee: Akron General Partners, Inc., Akron, OH (US)

( * ) Notice: Subject to any disclaimer, the term of this patent is extended or adjusted under 35 U.S.C. 154(b) by 77 days.

(21) Appl. No.: 14/251,083

(22) Filed: Apr. 11, 2014

(65) Prior Publication Data

US 2014/0309500 A1    Oct. 16, 2014

Related U.S. Application Data

(60) Provisional application No. 61/811,147, filed on Apr. 12, 2013.

(51) Int. Cl.
*A61B 17/02* (2006.01)
*A61B 17/00* (2006.01)

(52) U.S. Cl.
CPC ...... *A61B 17/0206* (2013.01); *A61B 2017/00526* (2013.01); *Y10T 29/49895* (2015.01)

(58) Field of Classification Search
CPC ........ A61B 1/32; A61B 17/02; A61B 17/0206
See application file for complete search history.

(56) References Cited

U.S. PATENT DOCUMENTS 3,965,890 A * 6/1976 Gauthier ............ A61B 17/0293
403/79
4,747,569 A * 5/1988 Hoshino ................ F16M 11/04
248/291.1

(Continued)

FOREIGN PATENT DOCUMENTS

EP         1652480 A1    5/2006
WO    2004/098416 A2   11/2004

OTHER PUBLICATIONS

PCT International Search Report and Written Opinion from International Application No. PCT/US2014/033804, mailed Aug. 14, 2014, 13 pages.

(Continued)

*Primary Examiner* — Ellen C Hammond
(74) *Attorney, Agent, or Firm* — Brouse McDowell; Heather M. Barnes; Michael G. Craig

(57) ABSTRACT

One or more techniques and/or systems are disclosed for a surgical device. A first paddle assembly may be engaged with a first paddle, and a second paddle assembly may be engaged with a second paddle. A first retainer arm assembly can be pivotally engaged with the first paddle assembly, and a second retainer arm assembly can be pivotally engaged with the second paddle assembly. A retaining key may be selectively engaged with the first and second retainer arm assemblies, and configured to couple the first retainer arm assembly and the second retainer arm assembly together in a pivotal arrangement; where the pivotal arrangement may to allow the first and second retainer arms to be positioned in a retained position with respect to each other; and may also allow the first and second retainer arm assemblies to be positioned in an non-retained position with respect to each other.

13 Claims, 15 Drawing Sheets

(56) References Cited

U.S. PATENT DOCUMENTS

| | | | | |
|---|---|---|---|---|
| 4,971,037 A | * | 11/1990 | Pelta | A61B 17/0206 403/390 |
| 4,993,862 A | * | 2/1991 | Pelta | A61B 17/0206 403/391 |
| 5,070,860 A | * | 12/1991 | Grounauer | A61B 17/0231 600/236 |
| 5,993,385 A | | 11/1999 | Johnston et al. | |
| 6,161,982 A | * | 12/2000 | Cole | B25B 13/481 403/298 |
| 6,409,731 B1 | | 6/2002 | Masson et al. | |
| 6,431,025 B1 | | 8/2002 | Koros et al. | |
| 6,663,562 B2 | | 12/2003 | Chang | |
| 7,018,332 B1 | | 3/2006 | Masson et al. | |
| 7,232,411 B2 | | 6/2007 | Dinkler, II et al. | |
| 7,566,302 B2 | | 7/2009 | Schwer | |
| 7,931,591 B2 | | 4/2011 | McCarthy et al. | |
| 7,955,257 B2 | | 6/2011 | Frasier et al. | |
| 7,988,625 B2 | | 8/2011 | Abdelgany et al. | |
| 2003/0060686 A1 | * | 3/2003 | Taylor | A61B 17/0206 600/210 |
| 2009/0182203 A1 | | 7/2009 | Hartnick et al. | |
| 2010/0185059 A1 | | 7/2010 | Sperling et al. | |
| 2012/0215072 A1 | | 8/2012 | Sperling et al. | |
| 2012/0296172 A1 | | 11/2012 | Raven, III et al. | |

OTHER PUBLICATIONS

Innomed, Brochure, 2 pages.
Innomed, Product Catalog, Jan. 2011, 52 pages.

* cited by examiner

SELF-RETAINING RETRACTOR

CROSS-REFERENCE TO RELATED APPLICATIONS

This application claims priority to Provisional Patent Application, U.S. Ser. No. 61/811,147, entitled SELF-RETAINING RETRACTOR, filed Apr. 12, 2013, which is incorporated herein by reference.

BACKGROUND

Retractors are commonly used during surgical procedures to provide access to a procedure site in the body. A retractor may provide surgical personnel with visual access to the procedure site as well as operational access, thereby enabling surgical personnel to use tools in site to perform the surgical procedure. Often, a retractor comprises one or more paddles or blades that are inserted into an opening at the procedure site, and used to spread tissue, and/or move organs or bones to create an access to a procedure location. In order to access the procedures site and insert the retractor(s), surgeons can make incisions at the skin and even further into an area to a surgical site.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As provided herein, a self-retaining retractor and/or bone elevator that may be used to retract target body tissue (e.g., and move bones and/or organs) and, for example, once locked into place, may be left in place, thereby mitigating additional interaction by surgical personnel until the retractor is moved or removed. Further, for example, at least a portion of the self-retaining retractor may be comprised of a radiolucent material that may allow sufficient radiological imaging output, resulting in a more desirable image of a procedure site (e.g., not, at least partially, blocked by the retractor).

In one implementation, a surgical device can comprise a first paddle assembly engaged with a first paddle, and a second paddle assembly engaged with a second paddle. Further, the surgical device can comprise a first retainer arm assembly pivotally engaged with the first paddle assembly, and a second retainer arm assembly pivotally engaged with the second paddle assembly. A retaining key can be selectively engaged with the first retainer arm assembly and the second retainer arm assembly, and the retaining key can be configured to operably couple the first retainer arm assembly and the second retainer arm assembly together in a pivotal arrangement.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

Figure 1:
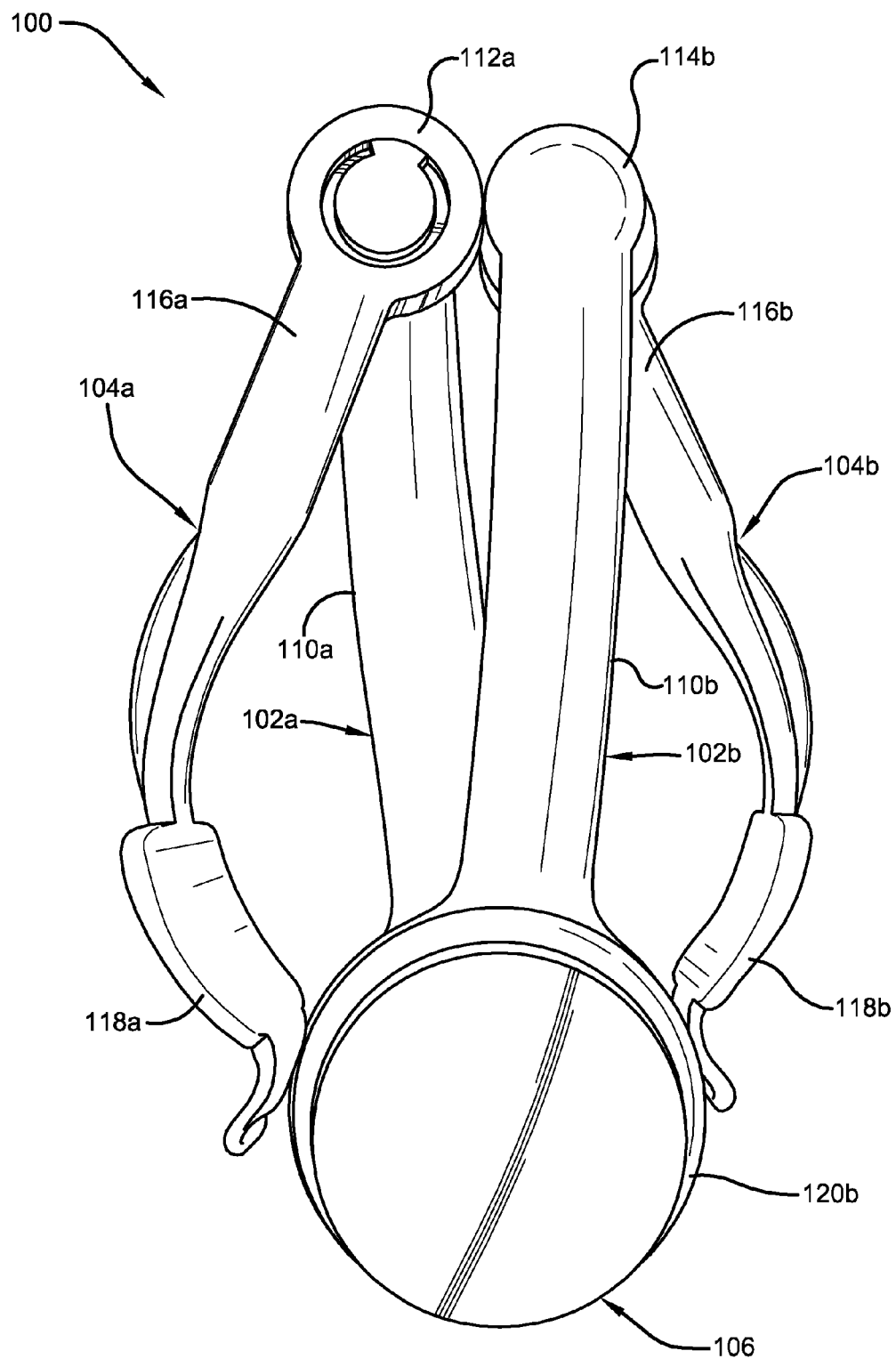
FIG. 1 is a component diagram illustrating an exemplary retractor device.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

During a surgical procedure, a surgeon can make one or more incisions into target body tissue (e.g., targeted for surgery or associated with the surgery) of a human or animal body in order to access a procedure site. Further, in order to obtain appropriate access to a procedure site, such as an organ, bone or other tissue, the surgeon may use a retractor to dilate or retract the skin, organs, and/or underlying layers of tissue. Typically, the purpose of a retractor is to provide access to the procedure site, and to protect soft tissue around the opening. Additionally, a different type of retractor, called an elevator, may be used to elevate a bone at the procedure site, such as to provide better access for performing the procedure.

Retractors comprise a variety of styles, shapes and sizes, appropriate for their specific function. Retractors often comprise surgical steel (e.g., or other types of metals and combinations of metals such as stainless steel), plastics, composites, and other appropriate materials, with one or more projections, generally termed "blades" or "paddles," used to retain an area of target body tissue, including bone, adjacent to the procedure site. A retracting paddle can comprise a variety of shapes, sizes and configurations, such as straight, curved, closed-end, open-end, etc. For example, when designed for use with long bones, the paddle may include a blunt or pointed distal projection (e.g., paddle end) used to engage with the bone, and to retract the skin and tissue. A simple retractor may include only a blade attached to a handle.

A hand-held retractor can be operated by the surgeon in one hand while using the other hand to perform other functions, such as positioning another retractor or performing the surgical procedure. Commonly, a second person may operate (e.g., position and/or hold) the one or more retractors while the surgeon performs the procedure. During some surgical procedures, the procedure site, such as a bone, may need to be imaged (e.g., using x-rays), for example. In this example, stainless steel (e.g., and other metal) components of a retractor, and/or a surgical assistant operating the retractor(s), may block portions of the procedure site in a resulting image, and/or the surgical assistants may be exposed to imaging radiation. Further, having an additional person in the operating theatre during the procedure can limit critical space for a surgeon(s) to operate.

A self-retaining retractor and/or bone elevator may be devised that can be used to retract target body tissue (e.g., targeted for surgery or associated with the surgery), for example, mitigating the need for an individual to hold the retractor in place during a desired procedure. Further, in one implementation, at least a portion of the self-retaining retractor may be comprised of a radiolucent material, which may appear relatively translucent in an image resulting from radiographic imaging of a procedure site while using the retractor. In another implementation, the self-retaining retractor may be comprised entirely of one or more metals (e.g., surgical steel, stainless steel, metal alloys, etc.), or combinations thereof. In another implementation, a first portion (e.g., retainer arms and assemblies) of the retractor may comprise a first material (e.g., metal), and a second portion (e.g., paddles) may comprise a second material (e.g., an imaging translucent polymer).

Figure 2:
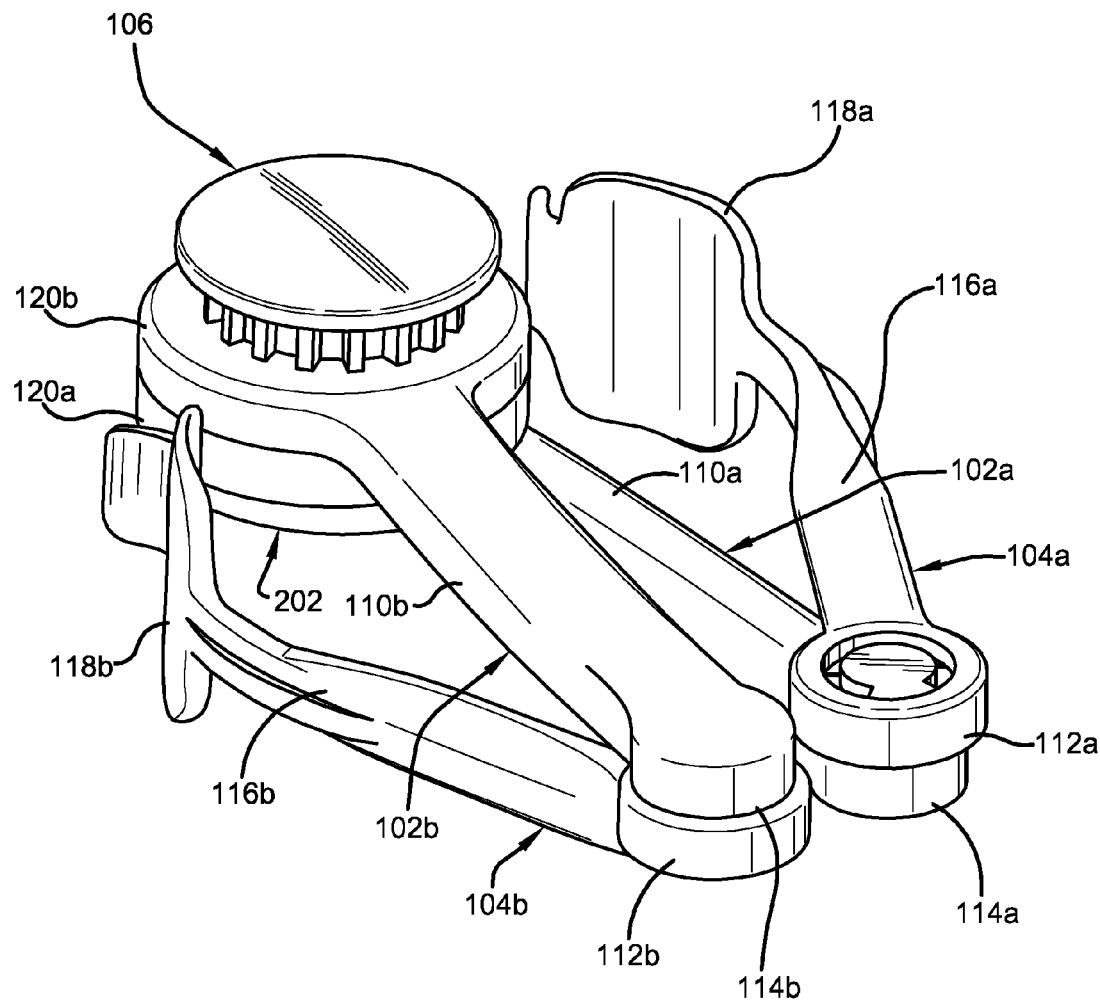
FIG. 2 is a component diagram illustrating a perspective view of an example retractor device.
Figure 3:
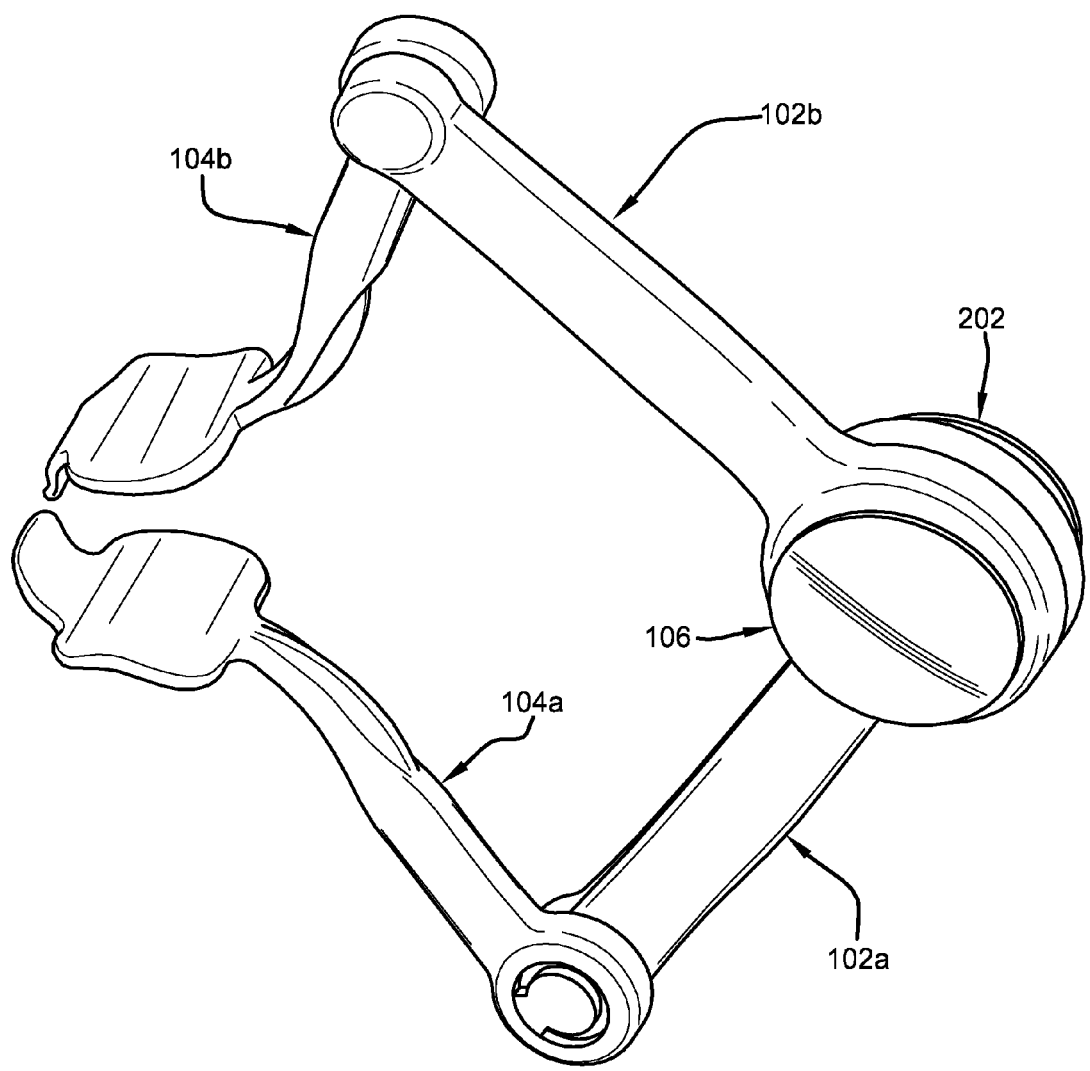
FIG. 3 is a component diagram illustrating a perspective view of an example retractor device.

FIGS. 1-3 are component diagrams illustrating an exemplary retractor device 100. The exemplary retractor device 100 comprises a first paddle assembly 104a and a second paddle assembly 104b. The first paddle assembly 104a is engaged with a first paddle 118a, and comprises a first paddle arm 116a and a first retainer arm engagement assembly 112a. The second paddle assembly 104b is engaged with a second paddle 118b, and comprises a second paddle arm 116b and a second retainer arm engagement assembly 112b.

Further, the exemplary retractor device 100 comprises a first retainer arm assembly 102a and a second retainer arm assembly 102b. The first retainer arm assembly 102a is pivotally engaged with the first paddle assembly 104a, and comprises a first retainer arm 110a, a first paddle engagement assembly 114a, and a first key engagement assembly 120a. The second retainer arm assembly 102b is pivotally engaged with the second paddle assembly 104b, and comprises a second retainer arm 110b, a second paddle engagement assembly 114b, and a second key engagement assembly 120b.

Additionally, the exemplary retractor device 100 comprises a retaining key 106, which can be selectively engaged with the first retainer arm assembly 102a and with the second retainer arm assembly 102b. The retaining key 106 can be configured to operably couple the first retainer arm assembly 102a and the second retainer arm assembly 102b together in a pivotal arrangement. The pivotal arrangement of the first retainer arm assembly 102a and the second retainer arm assembly 102b, using the retaining key 106, can comprise a first engagement that is configured to dispose the first and second retainer arm assemblies in a retained position with respect to each other. That is, for example, when the first retainer arm assembly 102a and the second retainer arm assembly 102b are disposed in the first engagement, using the retaining key 106, the respective retainer arms 110 may be disposed in a locked position, such that the respective arm assemblies 102 do not rotate around the pivot point located at the engagement location of the respective key engagement assemblies 120.

The pivotal arrangement can also comprise a second engagement position that is configured to disposes the first and second retainer arm assemblies in a non-retained position with respect to each other. That is, for example, when the first retainer arm assembly 102a and the second retainer arm assembly 102b are disposed in the second engagement (e.g., released from engagement with the retaining key 106) the respective retainer arms 110 may be disposed in a unlocked position, such that the respective arm assemblies 102 can freely rotate around the pivot point located at the engagement location of the respective key engagement assemblies 120.

In one implementation, the exemplary retractor device 100 can comprise a plug 202, which may be configured to be engaged with the retaining key 106, for example, to retain the first and second retainer arm assemblies 102 in the pivotal arrangement. As an example, the respective key engagement assemblies 120 may be selectively, slidably engaged with the retaining key 106. That is, for example, one or more teeth (e.g., or keys, or protrusions, etc.) disposed on the outer perimeter surface of the retaining key 106 may be aligned with one or more corresponding voids (e.g., and vice versa) disposed on the inner surface of the key engagement assemblies 120. In this example, the respective key engagement assemblies 120 may be selectively slide on and off the retaining key 106, and/or the retaining key 106 may be selectively slide in and out of the respective key engagement assemblies 120. In this implementation, for example, plug 202 may be selectively engaged with the retaining key 106, in order to mitigate disengagement of the respective key engagement assemblies from the retaining key 106.

Figure 4:
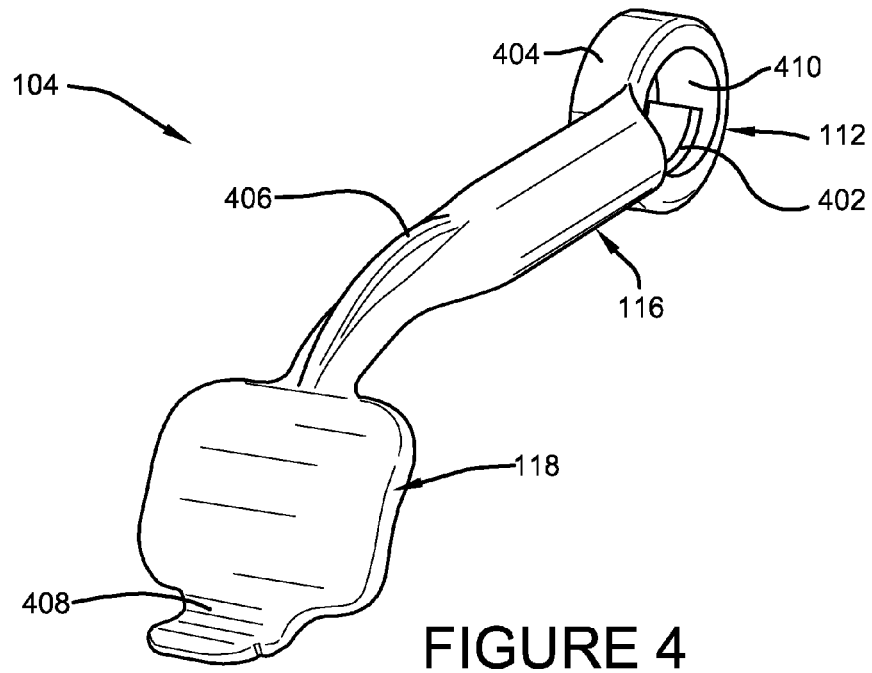
FIG. 4 is a component diagram illustrating one or more portions of an example retractor device.
Figure 5A:
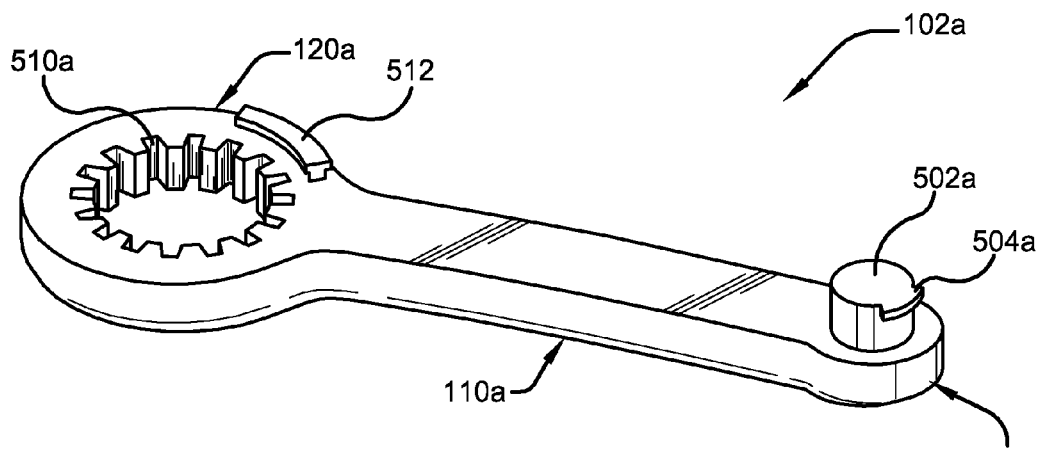
FIGS. 5A and 5B are component diagrams illustrating one or more portions of an example retractor device.
Figure 5B:
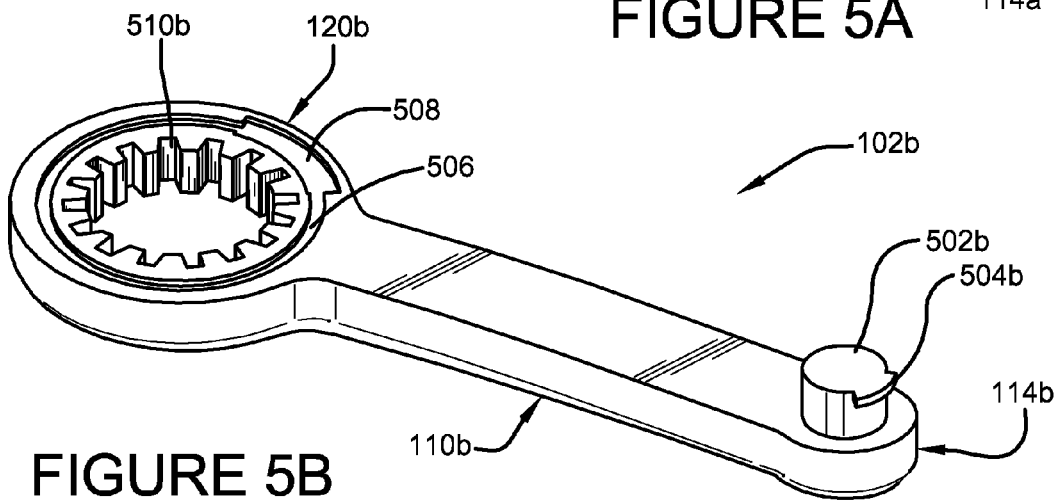

FIGS. 4, 5A and 5B are component diagrams illustrating one or more portions of an example retractor device. In FIG. 4, with continued reference to FIGS. 1-3, an example implementation of a paddle assembly 104 can comprise a paddle arm 116, a paddle 118 and a retainer arm engagement assembly 112. In FIG. 5A, an example implementation of a first retainer arm assembly 102a can comprise a first retainer arm 110a, a first paddle engagement assembly 114a, and a first key engagement assembly 120a. In FIG. 5B, an example implementation of a second retainer arm assembly 102b can comprise a second retainer arm 110b, a second paddle engagement assembly 114b, and a second key engagement assembly 120b.

In one implementation, in FIGS. 4, 5A and 5B, the retainer arm engagement assembly 112, of the paddle assembly 104, can comprise an annular shaped bearing component 404, having a female configuration to receive a corresponding male component 502a, 502b disposed on a retaining arm assembly 102a, 102b. That is, for example, the bearing component 404 may comprise an interior portion (e.g., a hole), disposed at least partly (e.g., or completely) through the thickness of the bearing component 404; and the corresponding male component 502a, 502b can be configured to fit into the interior portion of the bearing component 404.

Further, in one implementation, the bearing component 404 can comprise a bearing ridge 402, disposed in the interior portion of the bearing component 404, and configured to engage a complimentary protrusion 504a, 504b disposed on the male component 502a, 502b of the retaining arm assembly 102a, 102b. In this implementation, the interior portion of the bearing component 404 may comprise a receiving slot 410, disposed between portions of the bearing ridge 402, thereby creating a gap in the bearing ridge 402. The receiving slot 410 can be configured to receive the protrusion 504a, 504b disposed on the male component 502a, 502b of the retaining arm assembly 102a, 102b. That is, for example, the receiving slot 410 may be sized to fit merely a dimension (e.g., the width) of the protrusion 504a, 504b when inserted in a desired way.

Figure 6:
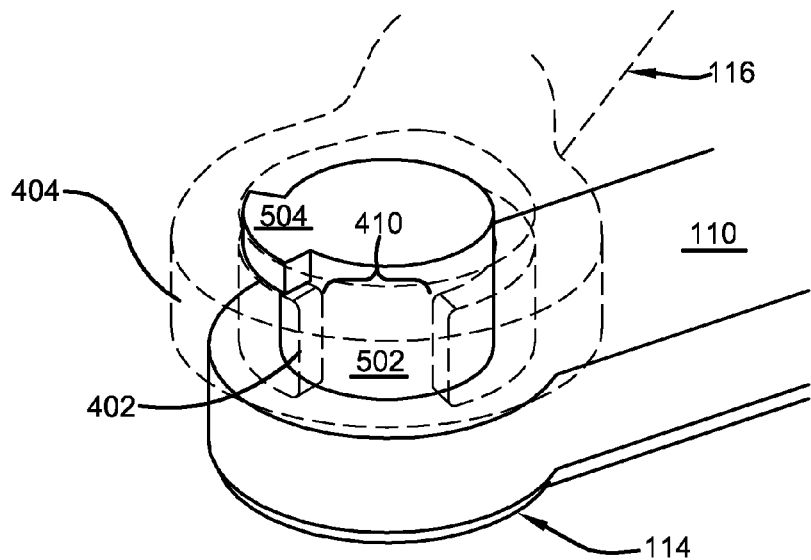
FIG. 6 is a component diagram illustrating one or more implementations of one or more portions of an example retractor device described herein.

As an illustrative example, as shown in FIG. 6 and with continued reference to FIGS. 1-5, the male component 502 may be pivotally engaged with the bearing component 404 by lining up the protrusion 504 with the receiving slot 410 disposed in the interior portion of the bearing component 404, and inserting the male component 502 into the bearing component 404. In this illustrative example, the bearing ridge 402 may comprise an internal dimension (e.g., having an annular shape corresponding to the cylindrical shape of the male component 502) that merely accommodates the external dimension of the male component 502. Further, a distance between an underside of the protrusion 504 and a top surface of the retainer arm(s) 110 may be so dimensioned to accommodate a height of the bearing ridge 402. As an example, the underside of the protrusion 504 may engage a top surface of the bearing ridge 402, such that a top surface of the male component and protrusion 504 are substantially aligned with a top surface of the bearing component 404 (e.g., relatively flush, so that the neither the protrusion 504 nor male component 502 may protrude above the top of the bearing component 404).

In this way, for example, when the male component 502 is inserted into the bearing component 404, the underside of the protrusion 504 may engage with a top surface of the bearing ridge when the paddle arm 116 and/or the retainer arm 110 are pivoted with respect to each other. In one implementation, one or more portions of the paddle assembly 104 and/or one or more portions of the retainer arm assembly 102 may be configured to merely allow the protrusion 504 to line up with the receiving slot 410 in a desired arrangement. That is, for example, a shape, dimension, and/or arrangement of the respective paddle assemblies 104a, 104b and retainer arm assemblies 102a, 102b may be configured to merely allow the respective corresponding protrusions and receiving slots line up in a desired arrangement. In this way, for example, the exemplary retractor 100 may merely be assembled in a desired configuration that is effective for the desired use; and/or so that unintentional disengagement of the respective paddle assemblies 104a, 104b and retainer arm assemblies 102a, 102b is mitigated during set-up and/or during a surgical procedure.

Returning to FIG. 4, in one implementation, a paddle rib 406 may be disposed on the paddle arm 116 of the paddle assembly 104. The paddle rib 406 may be configured to provide reinforcement and/or support to the associated paddle arm 116. As an example, respective paddle arms 116 may be subjected to bending stress (e.g., flexure) along the longitudinal axis of the arm due to a load being applied at respective ends of the paddle assembly 104. That is, for example, when a paddle end 408 is engaged against a bone, a downward load may be applied at the paddle end 408; and when the self-retaining retractor 100 is locked into a retained position, a downward force may be applied at the bearing component 404 end of the paddle assembly 104. In this example, the bending stress may be applied at the area comprising the paddle rib 406, which may provide additional reinforcement to mitigate potential stress-related failure at that point. In one implementation, the paddle rib 406 may be comprised of a same material as the paddle arm 116. In another implementation, the paddle rib may be comprised of a different material, such as metal, than that of the paddle arm 116, such as a polymer or different metal.

In FIGS. 5A and 5B, in one implementation, the first key engagement assembly 120a and the second key engagement assembly can respectively comprise an annular shape, and respectively comprise a through hole disposed therein. In this implementation, an internal surface 510a, 510b of the key engagement assembly 120 can comprise a key engagement configuration. As one example, the internal surface 510a of the first key engagement assembly 120a, and the internal surface 510b of the second key engagement assembly 120b, can respectively comprise a plurality of key engagement components (e.g., teeth, keys or protrusions), such as configured in a female gear arrangement.

Further, the first key engagement assembly 120a can comprise a slot key 512 configured to engage with a retaining slot 506 disposed in the second key engagement assembly 120b of the second retaining arm assembly 102b. The second key engagement assembly 120b of the second retaining arm assembly 102b can comprise the retaining slot 506 disposed therein, disposed, at least partially, into the interior face of the second key engagement assembly 120b. Additionally, the retaining slot 506 may comprise an access cutout 508, which can be configured to receive the slot key 512, for example, thereby providing access for the slot key 512 to the retaining slot 506. That is, for example, the slot key 512 may merely engage with the retaining slot 506 by inserting the slot key 512 into the access cutout 508. As one example, the access cutout 508 may be so dimensioned to merely fit the dimensions of the top portion of the slot key 512 in a desired alignment.

Figure 7:
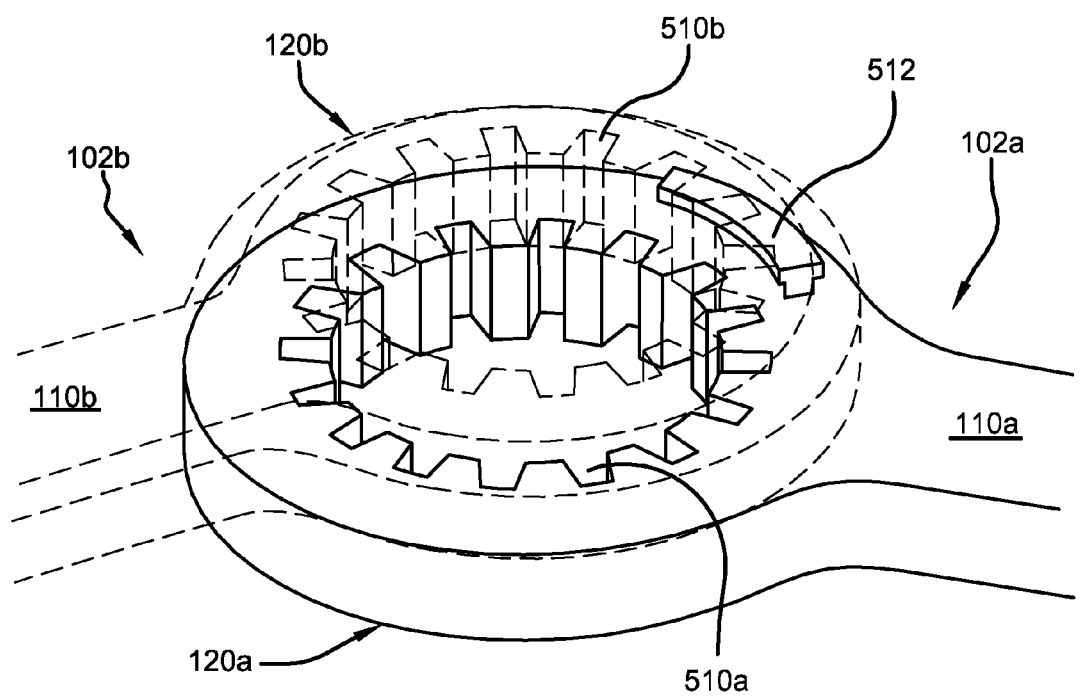
FIG. 7 is a component diagram illustrating one or more implementations of one or more portions of an example retractor device described herein.

As an illustrative example, as shown in FIG. 7 and with continued reference to FIGS. 5A and 5B, the first key engagement assembly 120a may be engaged with the second key engagement assembly 120b by aligning the slot key 512 on the interior face of the first retaining arm assembly 102a with the access cutout 508 on the interior face of the second retaining arm assembly 102b. In this example, the slot key 512 can be inserted into the access cutout 508, and the slot key 512 may be slide into the retaining slot 506, such as by rotating the first key engagement assembly 120a with respect to the second key engagement assembly 120b (e.g., or vice versa, or rotating both). In this way, for example the first key engagement assembly 120a and the second key engagement assembly 120b may be selectively engaged with each other, such that the respective first retaining arm assembly 102a and second retaining arm assembly 102b may not inadvertently disengage during a procedure. It will be appreciated that the implementations described herein are merely examples of a mechanism for mitigating undesired disengagement of the first and second key engagement assemblies. It is anticipated that those skilled in the art may design alternate arrangements and/or mechanisms for mitigating disengagement, for example, using different arrangements of keys and slots, a plurality of engagement keys, magnets, or some other attachment arrangement.

Figure 8:
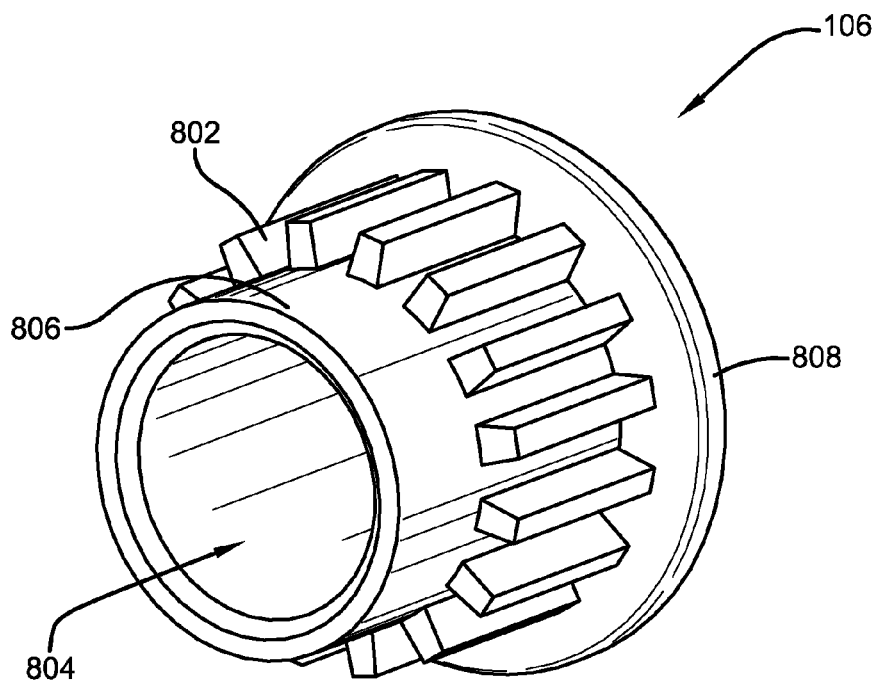
FIG. 8 is a component diagram illustrating one or more portions of an example retractor device.
Figure 9:
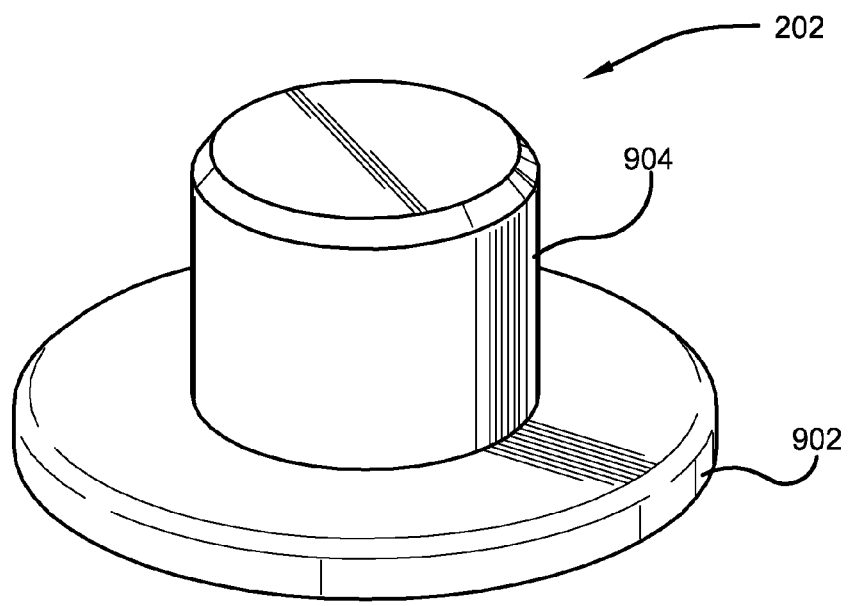
FIG. 9 is a component diagram illustrating one or more portions of an example retractor device.

Now with reference to FIGS. 8 and 9, and with continued reference to FIGS. 5A, 5B and 7, in one implementation, the retaining key 106 can comprise a key head 808 disposed at a first end, which may be configured to provide a mechanical stop for the retaining key 106, for example, when it is inserted into, and/or engaged with, the first and second key engagement assemblies 120. Further, in this implementation, the retaining key 106 can comprise one or more arm engagement elements 802 (e.g., teeth), which may be configured to selectively engage one or more of the first inner surface 510a of the first key engagement assembly 120a, and the second inner surface 510b of the second key engagement assembly 120b. As an example, the one or more arm engagement elements 802 (e.g., teeth) may slidably, selectively engage with one or more corresponding retainer arm assembly engagement elements (e.g., key engagement elements, such as a corresponding female portion) of one or more of the first inner surface 510a of the first key engagement assembly 120a, and the second inner surface 510b of the second key engagement assembly 120b. Additionally, as an example the key head 808 may comprise a mechanical stop for one or more of the key engagement assemblies 120, such that they are retained on the retaining key 106.

In FIG. 9, the plug 202 may comprise a plug head 902 disposed at a first end, which may be configured to provide a mechanical stop for the plug 202, for example, when it is inserted into the retaining key 106. Additionally, as an example, the plug head 902 may comprise a mechanical stop for the one or more of the key engagement assemblies 120, such that they are retained on the retaining key 106 when the plug 202 is engaged with the retaining key 106.

The plug 202 can comprise a plug insert 904 configured to be selectively inserted into, and removed from, a key opening 804 disposed in the retaining key 106. The plug insert 904 may be so dimensioned, and the key opening 804 may be so dimensioned, such that the plug insert 904 can be received by the key opening 804, for example, such that a the plug insert 904 may be rotated about its axis, but such that lateral movement within the key opening 804 is mitigated. That is, for example, the plug insert 904 should snuggly fit into the key opening 804. In one implementation, a plug locking means (not shown) may be provided, for example, such that the plug insert 904 may be selectively fixed (e.g., locked) into the key opening 804, thereby mitigating inadvertent removal of the plug insert 904 from the key opening 804.

In one implementation, as illustrated in FIG. 8, a plurality of arm engagement elements 802 (e.g., engagement means for engaging with engagement means disposed on one or both of the key engagement assemblies 120, such as protrusions and/or gear-like teeth) may be disposed substantially symmetrically around an outer surface of a key insert 806 of the retaining key 106. Further, in this implementation, the plurality of arm engagement elements 802 (e.g., teeth) may be disposed along a portion of the length of the key insert 806, such as from the key head 808 at the first end to a desired point on the key insert 806 located before a second end of the retaining key 106. That is, for example, the key insert 806 may comprise a portion without engagement elements, comprising no protrusions, and a portion comprising the arm engagement elements 802 (e.g., comprising teeth).

In one implementation, the portion of the key insert 806 comprising no engagement elements may be so dimensioned to accommodate a thickness of at least one of the first key engagement assembly 120a and the second key engagement assembly 120b. Further, in one implementation, the length of the portion comprising engagement elements 802 (e.g., comprising the arm engagement teeth 802) of the key insert 806 may be so dimensioned to accommodate at least a thickness of both the first key engagement assembly 120a and the second key engagement assembly 120b at a same time. In this way, for example, at least one of the first key engagement assembly 120a and the second key engagement assembly 120b may be disengaged from the toothed portion of the retaining key 106, thereby allowing the disengaged key engagement assembly 120 to rotate freely around the central axis of the retaining key 106, while remaining engaged with the retaining key 106 (e.g., stopped by the plug 202 from sliding off the retaining key 106).

Figure 10A:
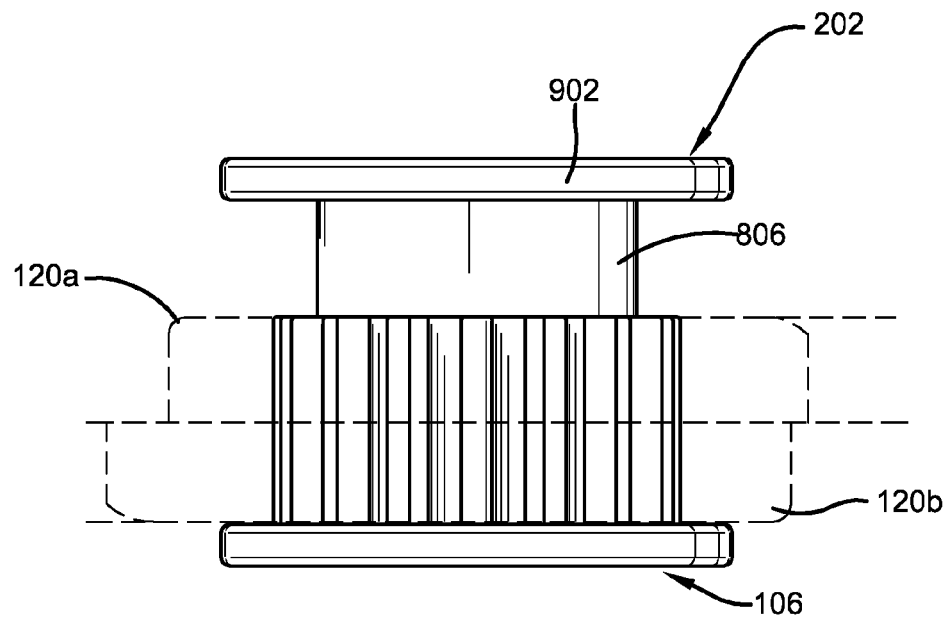
FIGS. 10A and 10B are component diagrams illustrating one or more implementations of one or more portions of an example retractor device described herein.
Figure 10B:
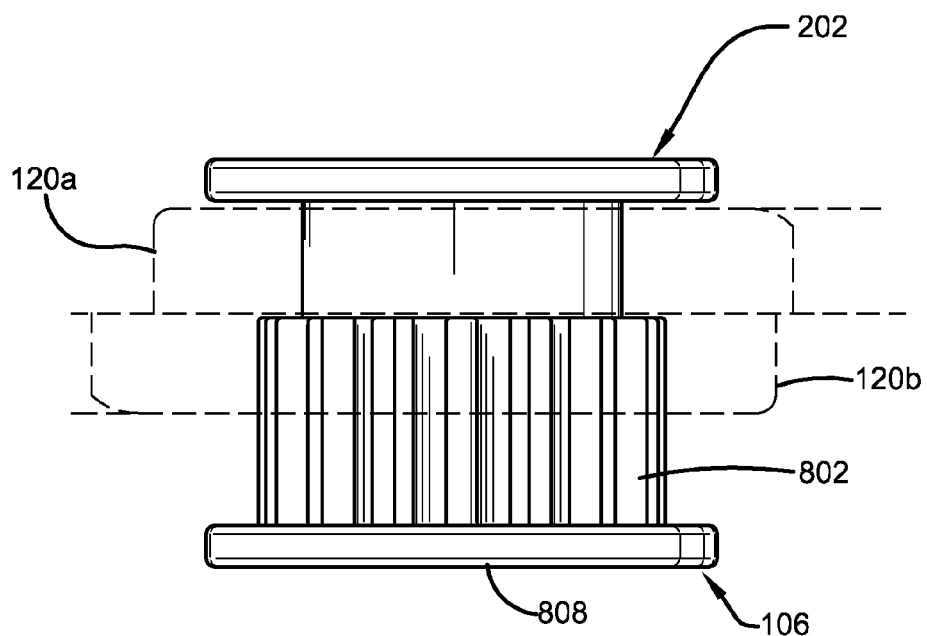
Figure 11:
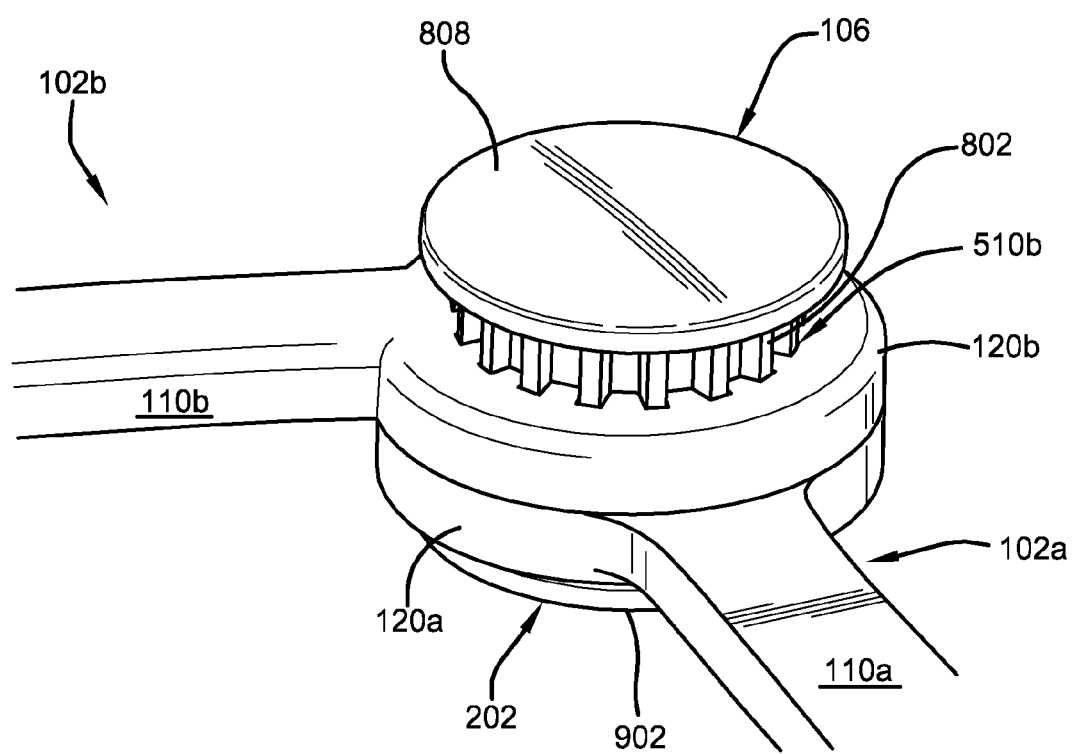
FIG. 11 is a component diagram illustrating one or more implementations of one or more portions of an example retractor device described herein.

As an illustrative example, as shown in FIGS. 10A, 10B and 11, the retaining key 106 may be inserted through the engaged first and second key engagement assemblies 120. Further, in this example, the plug 202 can be engaged with the retaining key 106. In FIG. 10A, the first and second key engagement assemblies 120 may be disposed at the portion of the key insert 806 comprising the engagement elements 802, for example, such that the first internal surface 510a and the second internal surface 510b are respectively engaged with the arm engagement elements 802. Additionally, as an example, the key head 808 may provide a stop, such that the first and second key engagement assemblies 120 may remain engaged with the retaining key 106 (e.g., and not slide off). In this way, for example, the first key engagement assembly 120a and the second key engagement assembly 120b may be locked in a desired position relative to each other, as the engagement of the internal surfaces 510 of the key engagement assemblies 120 with the arm engagement elements 802 of the retaining key 106 may mitigate rotation of either key engagement assemblies 120 around the axis of the retaining key 106.

In FIGS. 10B and 11, the first and second key engagement assemblies 120 can be moved (e.g., slid) toward the plug 202 (e.g., second end of the retaining key 106). In this example, the second key engagement assembly 120b may remain engaged with the arm engagement elements 802 (e.g., teeth) of the retaining key, while the first key engagement assembly 120a may be disposed at the portion of the key insert 806 without engagement elements. In one implementation, when the first key engagement assembly 120a is not engaged with the arm engagement elements 802 the portion of the key insert 806 without engagement elements may be so dimensioned to allow the first key engagement assembly 120a to rotate freely around the key insert 806. In this way, for example, a position of the first key engagement assembly 120a relative to the second key engagement assembly 120b may be adjusted to new desired position. Further, as an example, when the new desired position is reached the first and second key engagement assemblies 120 may be moved back toward the key head 808, such that the first and second key engagement assemblies 120 are selectively locked into the new desired position (e.g., as in FIG. 10A).

Figure 12A:
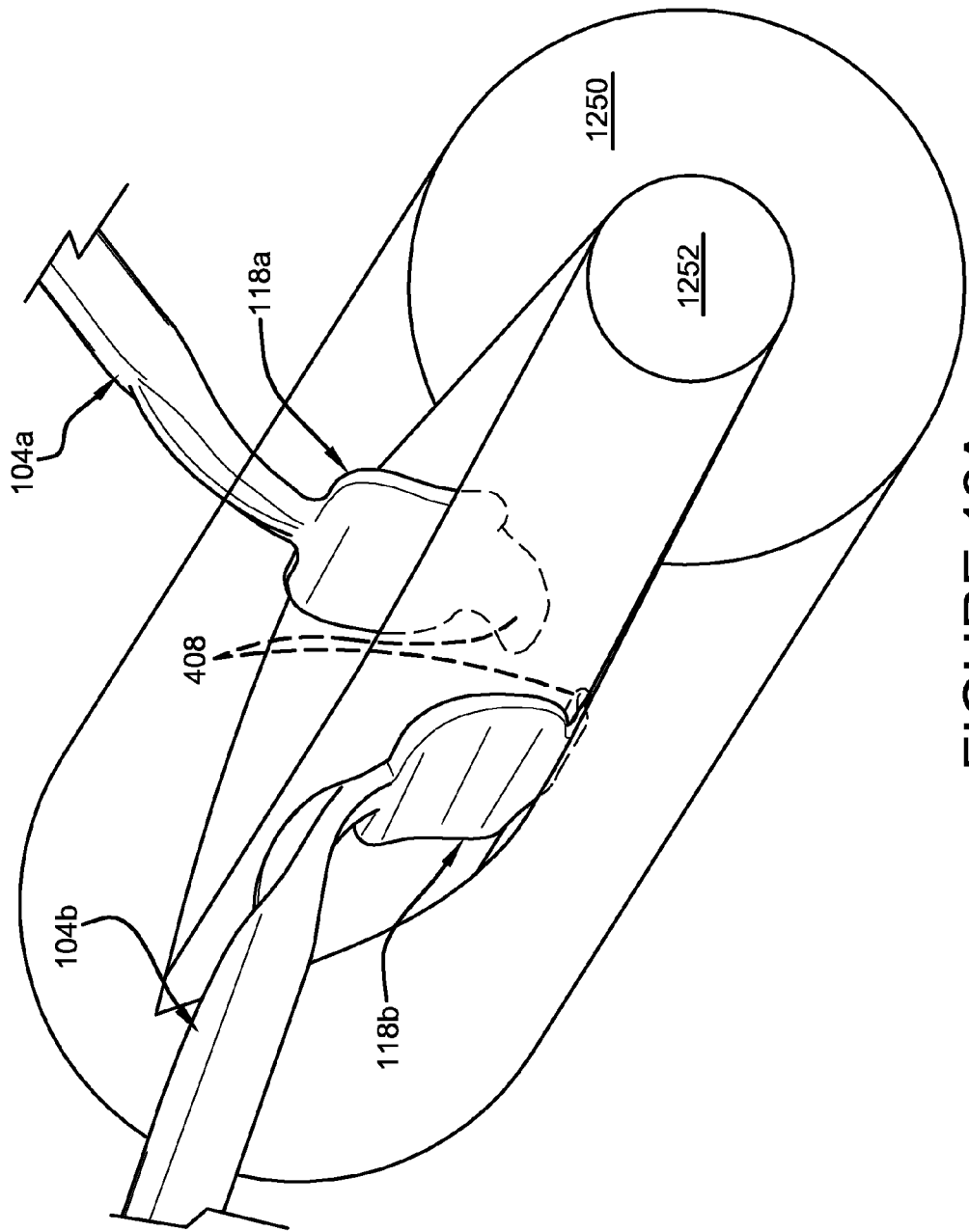
FIGS. 12A and 12B are component diagrams illustrating one or more implementations of one or more portions of an example retractor device described herein.
Figure 12B:
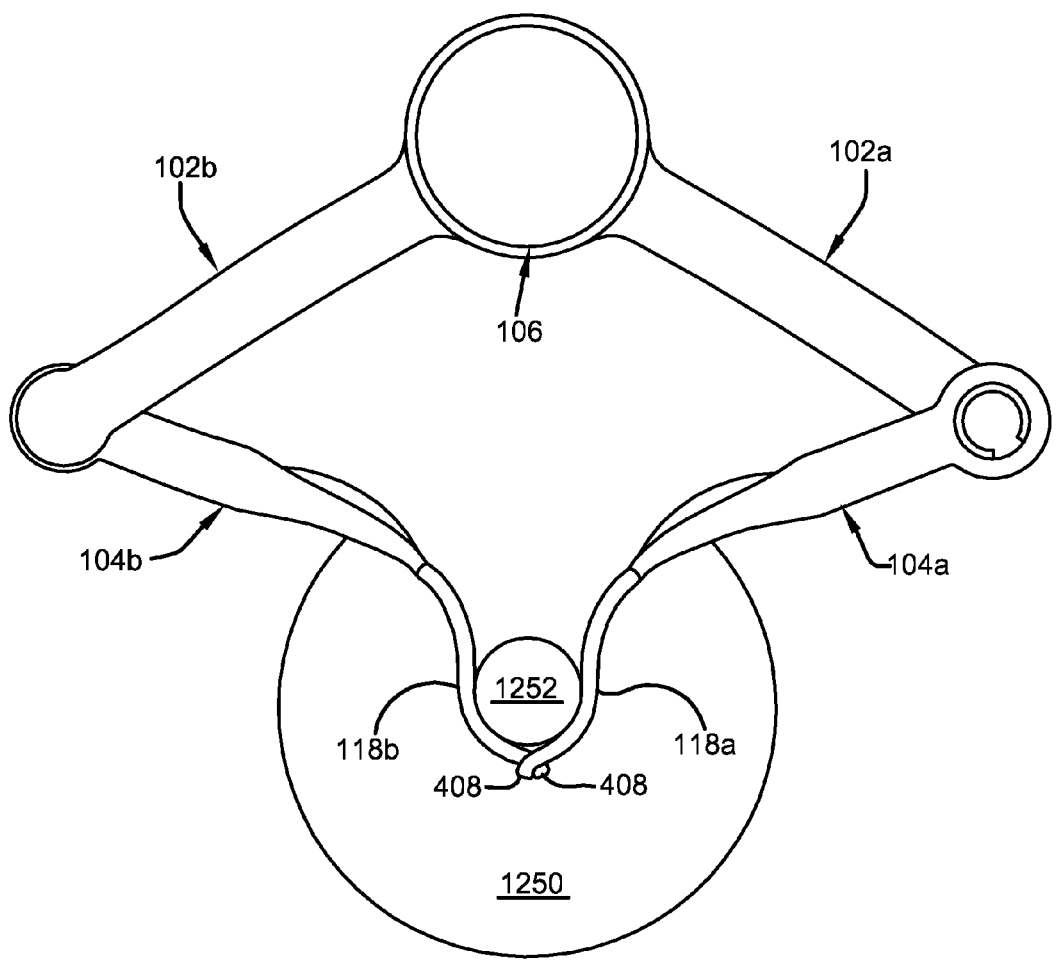

Now with reference to FIGS. 4, 12A and 12B, and continued reference to FIGS. 1-3, in one aspect, the paddle end 408 may comprise a size and/or shape that is configured to facilitate retraction of tissue, and/or elevation of a bone, during a procedure. Additionally, for example, the size and/or shape of the paddle 118 and/or paddle ends 408 (e.g., a first paddle end and second paddle end) may be configured to mitigate pressure to the target bone, and/or mitigate potential damage to the associated tissue when applied. As an example, in this aspect, current retractors and/or or bone elevators can comprise a variety of shapes and sizes designed for particular procedures on particular areas of the body. In one implementation, the paddle end 408 may be configured to engage with a long bone 1252 (e.g., femur), where one or more other portions of the paddle 118, and/or paddle arm 116, are configured to engage with the associated soft tissue 1250. That is, for example, the paddle end 408 may be sized and shaped to effectively engage the bone, such that a curvature of the paddle end 408 substantially matches the curvature of the target bone (e.g., to effectively keep it in place during the procedure). Further, in one implementation, different sized paddle ends 408 (e.g., and differently sized paddles) may be available for a same bone located in differently sized bodies (e.g., juveniles and adults).

In one implementation, the paddle 118, and/or paddle end 408, may be selectively removable from the paddle arm 116. In one implementation, the paddle arm 116 may be selectively removable from the paddle assembly 104. Further, as described above, the paddle assembly 104 is selectively removable from the retainer arm assembly 102. In this way, for example, a variety of paddle sizes and/or shapes may be available for use in desired procedures and/or for particular a particular patient. In one implementation, for example, the respective paddle assemblies 104 (e.g., and/or paddles 118, paddle ends 408, and/or paddle arms 116) may be selectively removed and replaced with the desired (e.g., appropriate) paddle assembly 104. In one implementation, a first paddle 118a may be removed from a first paddle arm 116a, and replaced with a third paddle. Further, in one implementation, the second paddle 118b may be removed from the second paddle arm 116b, and replaced with a fourth paddle.

As an illustrative example, in FIGS. 12A and 12B, the respective paddles 118a, 118b may be inserted into an opening in an area of a body where a procedure is planned. In this example, the paddle ends 408 are inserted under the bone 1252, where the shape and size of the paddle ends may substantially match the shape and size of the bone 1252. The paddles 118a, 118b and/or portions of the paddle arms 116a, 116b may engage with the tissue 1250 surrounding the bone 1252, for example, such that the tissue 1250 is disposed in a retracted position to provide an appropriate opening to perform the procedure; and/or the bone 1252 is elevated to place it in an appropriate position for the procedure.

Further, in one implementation, the respective retainer arm assemblies 102a, 102b may be selectively locked into a desired position, as described above, using the retaining key 106. In this way, for example, the self-retaining retractor 100 can be placed in the desired position, and may remain in the desired position during the procedure, while interaction with the retractor by an individual (e.g., surgical assistant, surgeon, nurse, etc.) is mitigated. As an example, the user (e.g., surgeon or assistant) may merely need to provide minimal support, or even no support, to the self-retaining retractor to remain in place. Additionally, in one implementation, the retractor 100 may be left in place during radiological imaging, as, at least a portion of, the retractor may be comprised of radiolucent materials, for example, and may appear to be substantially translucent on resulting images taken during the procedure.

Figure 13:
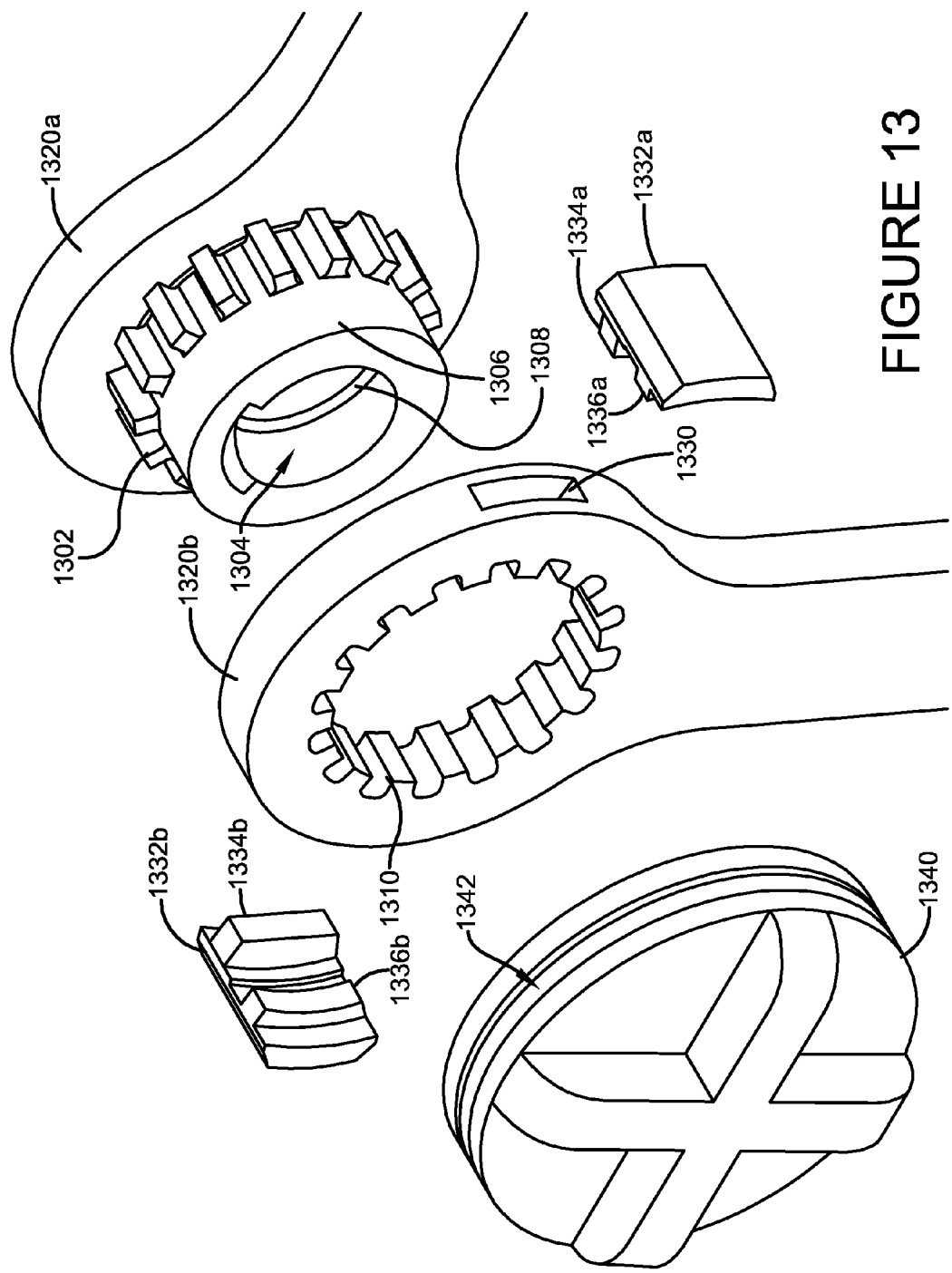
FIG. 13 is a component diagram illustrating one or more portions of an example implementation of one or more portions of the retractor device described herein.
Figure 14:
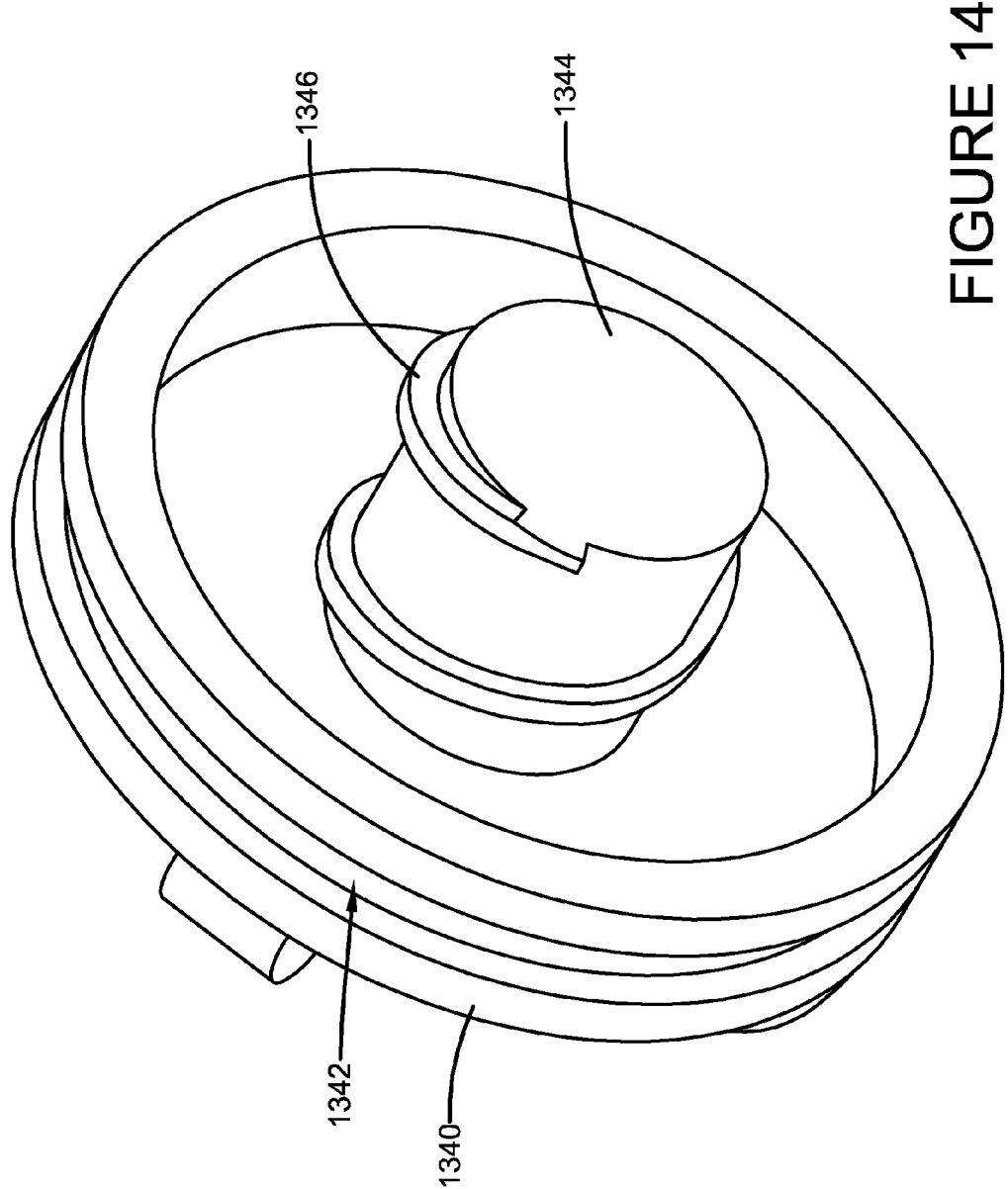
FIG. 14 is a component diagram illustrating one or more portions of an example implementation of one or more portions of the retractor device described herein.
Figure 15:
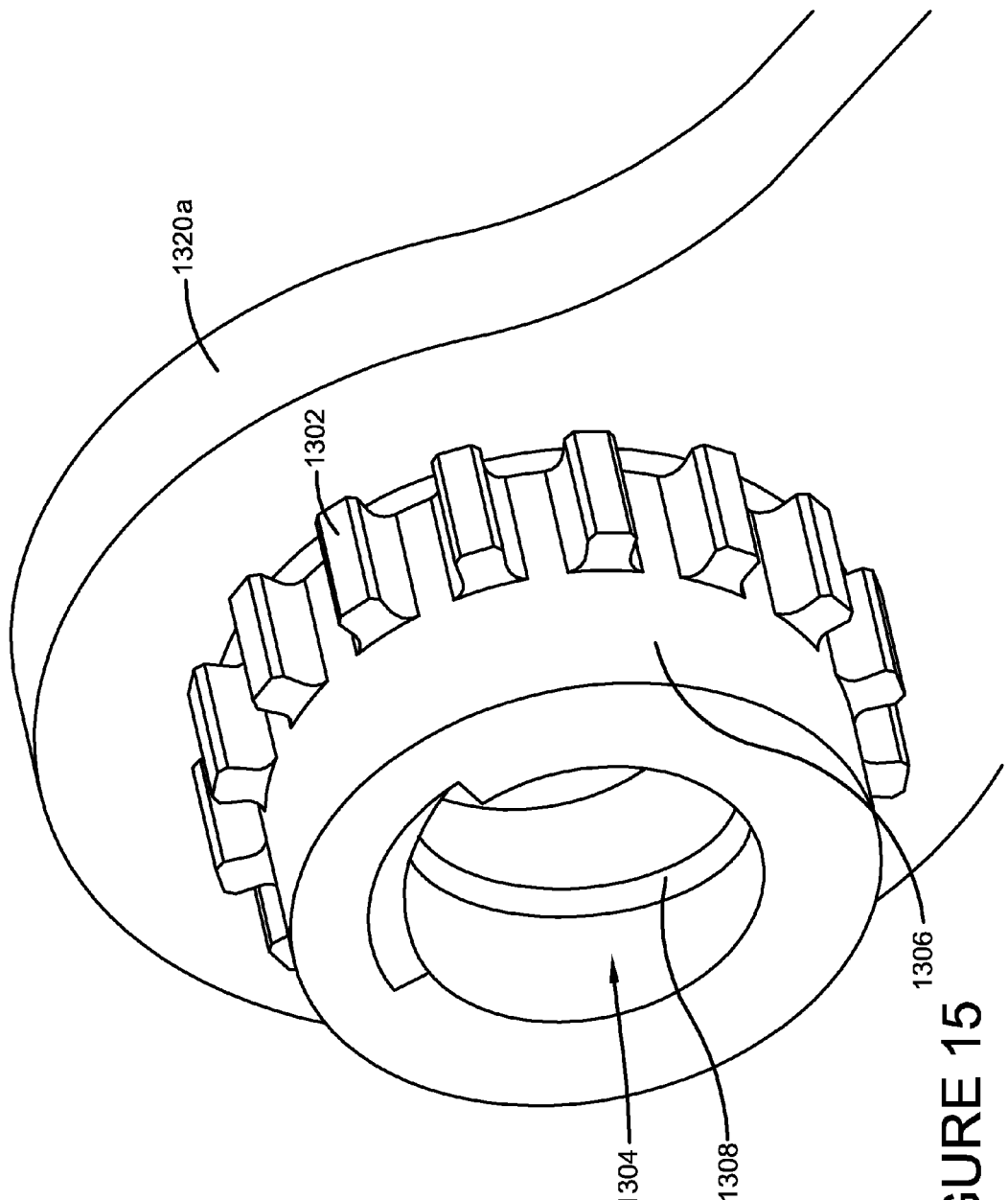
FIG. 15 is a component diagram illustrating one or more portions of an example implementation of one or more portions of the retractor device described herein.

Now with reference to FIGS. 13, 14, 15, 16 and 17, in one aspect, the two retainer arms (e.g., 110 of FIGS. 1-3) may be selectively engaged with each other using a variety of appropriate engagement means, selected using appropriate engineering techniques. FIGS. 13-17 illustrate one or more portions of an example implementation of a self-retaining retractor, which utilizes an alternate engagement means for the retainer arms. As illustrated in FIGS. 13 and 15, in one implementation, a first key engagement assembly 1320a (e.g., of a first retainer arm, such as 110a of FIGS. 1-3) may comprise a key insert 1306. For example, the key insert 1306 may be fixedly engaged with (e.g., formed with, attached to, fastened to, adhered to) the first key engagement assembly 1320a.

In this implementation, the key insert 1306 can comprise one or more arm engagement components 1302 (e.g., teeth), disposed around the perimeter (e.g., in a substantially uniform manner) of the key insert 1306. Further, the key insert 1306 can comprise a key opening 1304, comprising a hole that is disposed, at least partially (e.g., or fully), through the depth of the key insert 1306, and/or through the depth of the first key engagement assembly 1320a. In one implementation, the key opening 1304 may be disposed along the axis of rotation for the key engagement assemblies 1320, for example, when they are disposed in pivotal engagement with each other. In one implementation, the key opening 1304 may comprise female threads 1308, disposed around the interior wall of the key opening, and configured to receive corresponding male threads in selective, threaded engagement.

Figure 17:
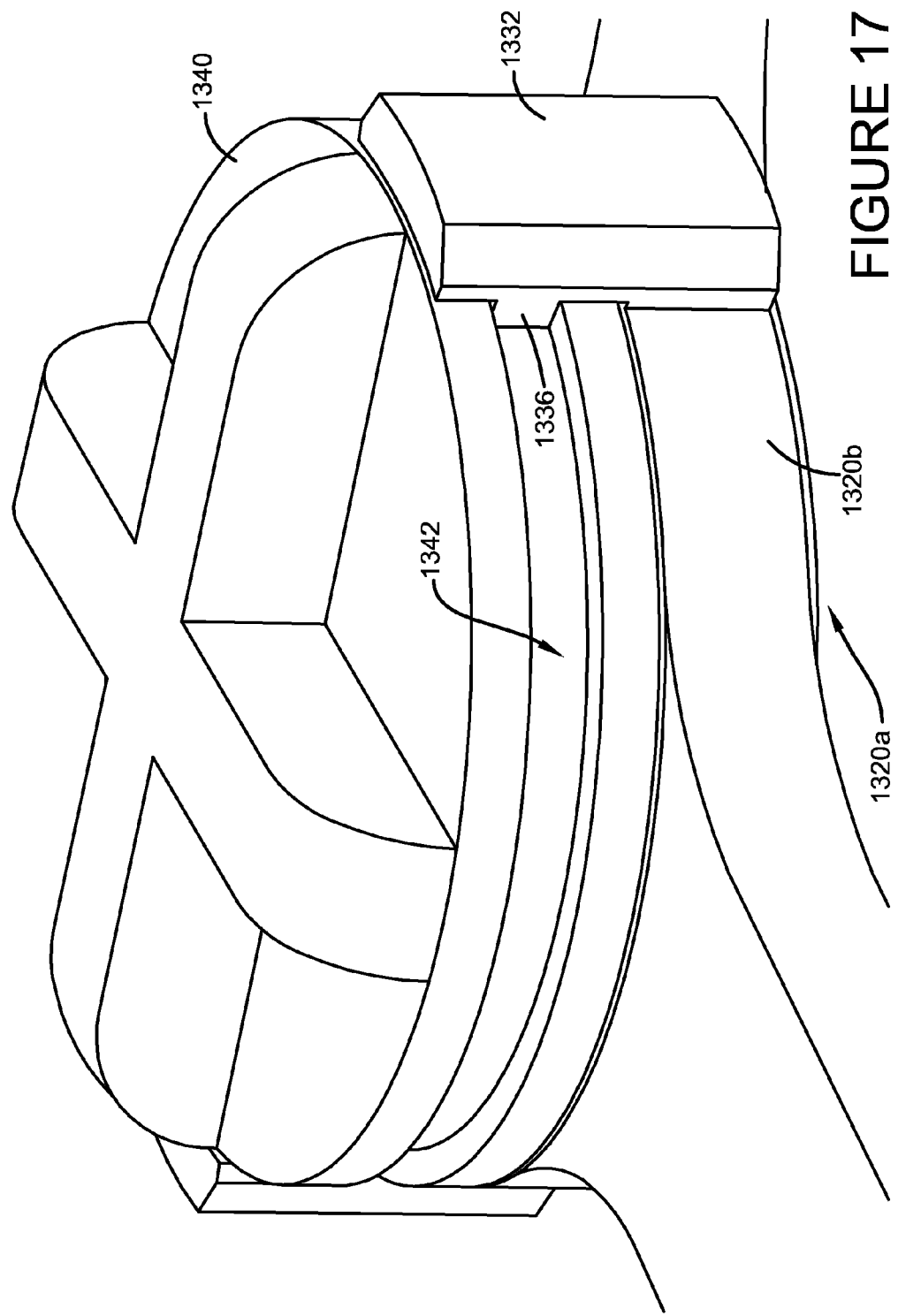
FIG. 17 is a component diagram illustrating one or more portions of an example implementation of one or more portions of the retractor device described herein.

As illustrated in FIGS. 13 and 17, in one implementation, a second key engagement assembly 1320b (e.g., of a second retainer arm, such as 110b of FIGS. 1-3) can comprise an internal surface 1310 of the second key engagement assembly 1320b. In this implementation, the internal surface 1310 can comprise a key engagement configuration, for example, comprising a plurality of key engagement components, such as teeth, keys or protrusions. As one example, the plurality of key engagement components may be configured in a female gear arrangement (e.g., for engaging a male gear arrangement of a corresponding part).

Figure 16:
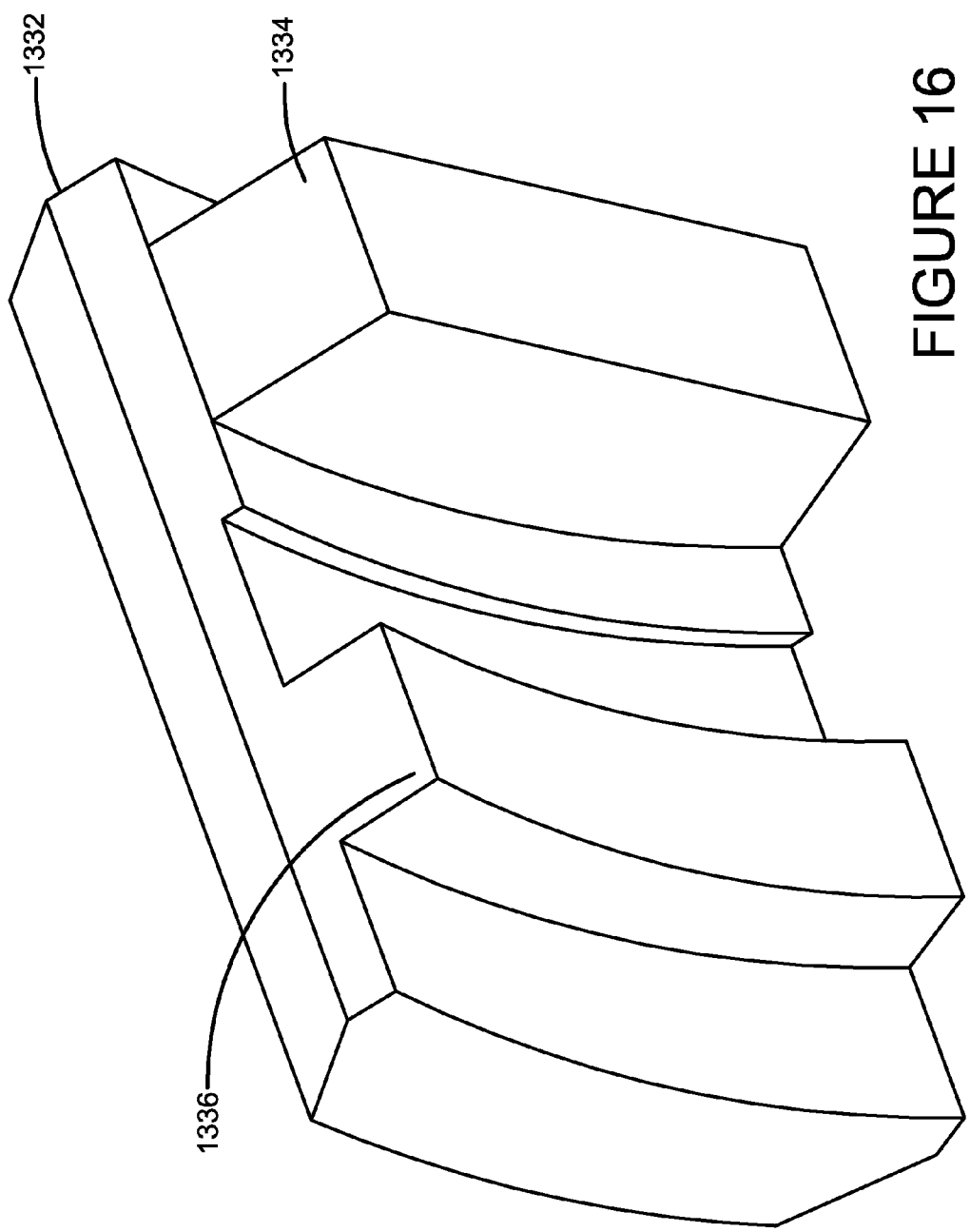
FIG. 16 is a component diagram illustrating one or more portions of an example implementation of one or more portions of the retractor device described herein.

In one implementation, as illustrated in FIGS. 13, 14, 16 and 17, the second key engagement assembly 1320b can comprise one or more arm retention slots 1330 (e.g., or holes, vias, inclusions, pockets, etc.), which may be configured to selectively receive at least a portion of an engagement retention component 1332. In one implementation, as illustrated in FIGS. 13, 16 and 17, a first engagement retention component 1332a may comprise s first arm engagement protrusion 1334a, and a first plug engagement protrusion 1336a. Further, in this implementation, a second engagement retention component 1332b may comprise a second arm engagement protrusion 1334b, and a second plug engagement protrusion 1336b.

In one implementation, as illustrated in FIGS. 13, 14 and 17, a threaded engagement plug 1340 can comprise a plug retention slot 1340, for example, comprising a type of bearing ridge, where the plug retention slot is configured to selectively engage with one or more of the first plug engagement protrusion 1336a and the second plug engagement protrusion 1336b (e.g., and a third plug engagement protrusion, etc.). Further, the threaded engagement plug 1340 can comprise a plug insert 1344, which comprises one or more male threads, and is configured to selectively engage with corresponding female threads, for example, such the female threads 1308 disposed in the key opening 1304 of the key insert 1306.

As an illustrative example, as illustrated in FIGS. 13-17, the key insert 1306 of the first key engagement assembly 1320a can be selectively engaged with (e.g., inserted into) the opening in the second key engagement assembly 1320b. Further, in this example, the one or more arm engagement components 1302 may be selectively engaged with the internal surface 1310 of the second key engagement assembly 1320b. For example, where the one or more arm engagement components 1302 comprise a male gear arrangement, they may be engaged with a female gear arrangement comprised in the internal surface 1310 of the second key engagement assembly 1320b. As an example, when the one or more arm engagement components 1302 are selectively engaged with the internal surface 1310 of the second key engagement assembly 1320b, the first and second key engagement assemblies 1320 may be disposed in a desired retained position, such that the respective retainer arms may not be pivoted with respect to each other. However, in this example, when the key insert 1306 portion that does not comprise the arm engagement components 1302 is engaged with the opening in the second key engagement assembly 1320b, the retainer arms may be pivoted with respect to each other.

Additionally, in the illustrative example, the plug insert 1344, of the threaded engagement plug 1340, may be selectively inserted into the key opening 1304 of the key insert 1306. As an example, the male threads 1346 disposed on the plug insert 1344 may be selectively engaged with the female threads 1308 disposed in the key opening 1304 of the key insert 1306. In this example, selective engagement can comprise rotating the threaded engagement plug such that the male threads 1346 can fully engage the female threads 1308, at least until the threaded engagement plug 1340 is seated in a desired arrangement (e.g., fully seated) with the key insert 1306, and therefore seated in a desired arrangement with the respective key engagement assemblies 1320. In one example, the threaded engagement plug 1340 may be rotated until the plug 1340 and respective key engagement assemblies 1320 are disposed in a retained position with respect to each other.

In one implementation, the first arm engagement protrusion 1334a, of the first engagement retention component 1332a, may be configured to selectively engage with (e.g., fit into) an arm retention slot 1330 disposed in the second key engagement assembly 1320b. Further, the second arm engagement protrusion 1334b, of the second engagement retention component 1332b, may be configured to selectively engage with another arm retention slot 1330 disposed in the second key engagement assembly 1320b, such as at an opposing side. In one implementation, the first and second arm engagement protrusions 1334a and 1334b may be fixedly engaged with their respective arm retention slots 1330. As an example, an arm engagement protrusion 1334 may be press fit into the arm retention slot 1330, such that the loosening of the engagement between the arm engagement protrusion 1334 and arm retention slot 1330 is mitigated (e.g., the engagement retention component 1332 is fixedly engaged with the key engagement assemblies 1320. In another implementation, the arm engagement protrusion 1334 may be fastened to the arm retention slot 1330, such as by a bonding agent (e.g., glue), welding, soldering, sonic welding, heat treatment, a fastener, or some other form of fastening.

In one implementation, the first plug engagement protrusion 1336a, of the first engagement retention component 1332a, may be configured to selectively engage with (e.g., fit into) the plug retention slot 1342 disposed in the threaded engagement plug 1340. Additionally, in this implementation, the second plug engagement protrusion 1336b, of the second engagement retention component 1332b, may be configured to selectively engage with (e.g., fit into) the plug retention slot 1342 disposed in the threaded engagement plug 1340.

In this way, for example, when the threaded engagement plug 1340 is fully engaged with (e.g., threaded into) the key opening 1304, such that the threaded engagement plug 1340, the first key engagement assembly 1320a, and the second key engagement assembly 1320b are fully engaged with each other, the first and/or second engagement retention components 1332 can be engaged with the threaded engagement plug 1340 and the second key engagement assembly 1320b, as illustrated in FIG. 17. As an example, engaging the respective engagement retention components 1332 with the threaded engagement plug 1340 and the second key engagement assembly 1320b may effectively, selectively retain the two retainer arms (e.g., 110 of FIGS. 1-3) in a desired, locked position during a procedure (e.g., surgery). As a further example, the selective retention of the two retainer arms (e.g., 110 of FIGS. 1-3) may be infinitely adjustable relative to each other, and the adjustment of one retainer arm (e.g. 110) to the other retainer arm (e.g. 110) may be performed with one hand of the user, while the other hand can be used to engage the threaded engagement plug 1340.

In another implementation, the use of the engagement retention components 1332 to selectively engage the second key engagement assembly 1320b may provide for selective adjustment of the second key engagement assembly 1320b with respect to the first key engagement assembly 1320a. That is, for example, unscrewing the threaded engagement plug 1340 may withdraw the plug insert 1344 from the key opening 1304. In this example, this unscrewing would also draw the threaded engagement plug 1340 away from the first key engagement assembly 1320a. In this implementation, because the second key engagement assembly 1320b is selectively engaged with the threaded engagement plug 1340 using the engagement retention components 1332, the second key engagement assembly 1320b can also be drawn away from the first key engagement assembly 1320a using the unscrewing motion. Further, as an example, once the internal surface 1310 of the second key engagement assembly 1320b is disengaged from the one or more arm engagement components 1302 of the key insert 1306, the first and second key engagement assemblies 1320 may be adjusted with respect to each other. Additionally, as an example, once a desired adjustment is attained, the threaded engagement plug 1340 may be screwed into the key opening 1304 to selectively re-engage the first and second key engagement assemblies 1320 in the desired arrangement.

In one or more implementations, the example devices and techniques, described herein, may be used in a variety of procedures both for humans and animals. As an example, procedures where one or more of the devices, described herein, can include, without limitation, ORIF (open reduction internal fixation) of proximal femur fractures, ORIF of femoral shaft fractures, ORIF of distal femur fractures, primary THA (total hip arthroplasty), revision THA, endoprosthesis, and ORIF of fractures of other long bones, such as the humerus and/or the tibia. Further, use of the self-retaining nature of the retractor device is not limited to merely those examples, listed above. It is anticipated that those skilled in the art may devise alternate uses for the retractor device in surgical procedures.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A surgical retractor device, comprising:
   a first paddle assembly comprising a first paddle arm, a first paddle disposed at a distal end of the first paddle arm, and a first retainer arm engagement assembly disposed at a proximal end of the first paddle arm;
   a second paddle assembly comprising a second paddle arm, a second paddle disposed at a distal end of the second paddle arm, and a second retainer arm engagement assembly disposed at a proximal end of the second paddle arm;
   a first retainer arm assembly comprising a first retainer arm, a first paddle engagement assembly disposed at a distal end of the first retainer arm, and a first key engagement assembly disposed at a proximal end of the first retainer arm, the first paddle engagement assembly selectably engaged with the first retainer arm engagement assembly in a first pivotal arrangement;
   a second retainer arm assembly comprising a second retainer arm, a second paddle engagement assembly disposed at a distal end of the second retainer arm, and a second key engagement assembly disposed at a proximal end of the second retainer arm, the second paddle engagement assembly selectably engaged with the second retainer arm engagement assembly in a second pivotal arrangement; and
   a retaining key selectably engaged with the first key engagement assembly and the second key engagement assembly, the retaining key coupling the first retainer arm assembly and the second retainer arm assembly together in a third pivotal arrangement, and the retaining key selectably locking the first retainer arm assembly and second retainer arm assembly together to mitigate pivoting during use, the first pivotal arrangement, second pivotal arrangement and the third pivotal arrangement respectively comprising axes parallel to each other.

2. The device of claim 1, the third pivotal arrangement comprising:
   a first engagement position configured to dispose the first retainer arm assembly and the second retainer arm assembly in a retained position with respect to each other; and
   a second engagement position configured to dispose[s] the first retainer arm assembly and the second retainer arm assembly in a non-retained position with respect to each other.

3. The device of claim 2, comprising a retracted position when the third pivotal arrangement is disposed in the first engagement position, and at least one of a first paddle end and a second paddle end are configured to engage with target body tissue.

4. The device of claim 2, at least a portion of the first paddle and at least a portion of the second paddle respectively configured to selectively engage a bone.

5. The device of claim 4, comprising a self-retaining retracted position when the first paddle and the second paddle are engaged with the bone, and the first retainer arm assembly and the second retainer arm assembly are engaged with the retaining key in the retained position.

6. The device of claim 1, at least one of the first paddle and the second paddle configured to engage with tissue to facilitate a surgical procedure.

7. The device of claim 6, at least one of the first paddle and the second paddle configured to engage with bone to provide an elevated bone position during a surgical procedure.

8. The device of claim 1, at least one of:
the first paddle assembly selectably removable from the first retainer arm assembly; and
the second paddle assembly selectably removable from the second retainer arm assembly.

9. The device of claim 8, at least one of:
the first retainer arm assembly configured to selectably engage with a third paddle assembly; and
the second retainer arm assembly configured to selectably engage with a fourth paddle assembly.

10. The device of claim 1, the first retainer arm assembly configured to be selectably disengaged from the first paddle assembly; and the second retainer arm assembly configured to be selectably disengaged from the second paddle assembly.

11. The device of claim 1, the retaining key, comprising:
a key head;
a key insert fixedly engaged with the key head, the key insert comprising a perimeter; and
a one or more engagement elements disposed around the perimeter of the key insert.

12. The device of claim 1, comprising a plug configured to selectably engage with the retaining key; a combination of the retaining key and plug configured to selectably retain the first retainer arm assembly and second retainer arm assembly in the pivotal arrangement.

13. An apparatus for facilitating a surgical retraction procedure, comprising:
a first retainer arm assembly;
a second retainer arm assembly;
a first paddle assembly engaged with a first paddle configured to engage target body tissue during a surgical procedure, the first paddle assembly configured to selectably engage with the first retainer arm assembly in a first pivotal arrangement;

a second paddle assembly engaged with a second paddle configured to engage target body tissue during a surgical procedure, the second paddle assembly configured to selectably engage with the second retainer arm assembly in a second pivotal arrangement;

a retaining key configured to selectively engage with the first retainer arm assembly and the second retainer arm assembly, the retaining key configured to operably couple the first retainer arm assembly and the second retainer arm assembly together in a third pivotal arrangement, the first pivotal arrangement, second pivotal arrangement and the third pivotal arrangement respectively comprising axes parallel to each other, the third pivotal arrangement comprising:

a first engagement position configured to dispose the first retainer arm assembly and the second retainer arm assembly in a locked position with respect to each other, to mitigate pivoting; and a second engagement position configured to dispose the first retainer arm assembly and the second retainer arm assembly in a non-locked position with respect to each other, to allow pivoting; and a plug configured to selectably engage with the retaining key configured to selectably retain the first retainer arm assembly and second retainer arm assembly in the third pivotal arrangement.

* * * * *